United States Patent
Barnell

(10) Patent No.: US 9,038,822 B2
(45) Date of Patent: May 26, 2015

(54) BLOW-MOLDED PACKAGE FOR A CATHETER

(71) Applicant: Medtronic Vascular, Inc., Santa Rosa, CA (US)

(72) Inventor: Jeffrey Barnell, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 14/157,279

(22) Filed: Jan. 16, 2014

(65) Prior Publication Data

US 2014/0262882 A1    Sep. 18, 2014

Related U.S. Application Data

(60) Provisional application No. 61/788,268, filed on Mar. 15, 2013.

(51) Int. Cl.
*A61M 25/00* (2006.01)
*B29C 49/00* (2006.01)
*B29C 49/42* (2006.01)
*B29L 23/00* (2006.01)
*B29L 31/00* (2006.01)

(52) U.S. Cl.
CPC .............. *A61M 25/002* (2013.01); *B29C 49/00* (2013.01); *B29C 49/4273* (2013.01); *B29L 2023/007* (2013.01); *B29L 2031/7542* (2013.01)

(58) Field of Classification Search
CPC .................................................... A61M 25/002
USPC .................... 206/364, 363, 438; 604/523, 533
See application file for complete search history.

(56) References Cited

U.S. PATENT DOCUMENTS

| | | | | |
|---|---|---|---|---|
| 5,125,416 A | * | 6/1992 | Phillips | 600/585 |
| 5,344,011 A | * | 9/1994 | DiBernardo et al. | 206/364 |
| 5,366,444 A | * | 11/1994 | Martin | 604/159 |
| 5,454,785 A | * | 10/1995 | Smith | 604/510 |
| 6,375,006 B1 | * | 4/2002 | Samuels | 206/364 |
| 6,902,057 B2 | | 6/2005 | Duffy | |
| 7,104,399 B2 | | 9/2006 | Duffy et al. | |

(Continued)

FOREIGN PATENT DOCUMENTS

| | | |
|---|---|---|
| EP | 2327444 | 6/2011 |
| WO | WO2004/022433 | 3/2004 |
| WO | WO2012/141826 | 10/2012 |

OTHER PUBLICATIONS

PCT/US2014/016542, PCT Search Report and Written Opinion, mailed Jun. 27, 2014.

*Primary Examiner* — Steven A. Reynolds

(57) ABSTRACT

A package for a medical device having an elongated shaft and a proximal luer fitting includes a one-piece body formed as a single structure via blow molding. The blow-molded one-piece body includes at least a spiral casing formed therein, the spiral casing defining a spiral lumen configured to receive the elongated shaft of the medical device. Webbing is disposed between adjacent curved portions of the spiral casing. The one-piece body formed via blow-molding may also include a removable reversible loading tube, a luer retainer, a cannula holder, one or more slots for attaching an information card thereto, a fastener for clipping the medical device thereto, and a compartment for holding an oxygen scavenger. Further, the one-piece body formed via blow-molding may include non-circular lumens and may be configured to receive multiple medical devices.

13 Claims, 16 Drawing Sheets

(56) References Cited

U.S. PATENT DOCUMENTS

| | | | |
|---|---|---|---|
| 7,334,678 B2 * | 2/2008 | Kesler et al. | 206/364 |
| 7,640,714 B2 * | 1/2010 | Waller et al. | 53/430 |
| 8,568,373 B2 * | 10/2013 | Kuniyasu et al. | 604/265 |
| 8,708,999 B2 * | 4/2014 | Hong et al. | 604/544 |
| 2004/0055926 A1 | 3/2004 | Duffy et al. | |
| 2005/0178684 A1 | 8/2005 | Kesler et al. | |
| 2005/0256501 A1 | 11/2005 | Rispens | |
| 2006/0278546 A1 * | 12/2006 | State et al. | 206/364 |
| 2006/0278547 A1 * | 12/2006 | Rowe et al. | 206/364 |
| 2008/0006554 A1 | 1/2008 | Duffy et al. | |
| 2008/0023346 A1 * | 1/2008 | Vonderwalde | 206/210 |
| 2011/0127186 A1 * | 6/2011 | Enns et al. | 206/364 |
| 2012/0172846 A1 * | 7/2012 | Nakamoto et al. | 604/533 |
| 2012/0261290 A1 | 10/2012 | Limjaroen et al. | |
| 2014/0144798 A1 * | 5/2014 | Benesh | 206/363 |

\* cited by examiner

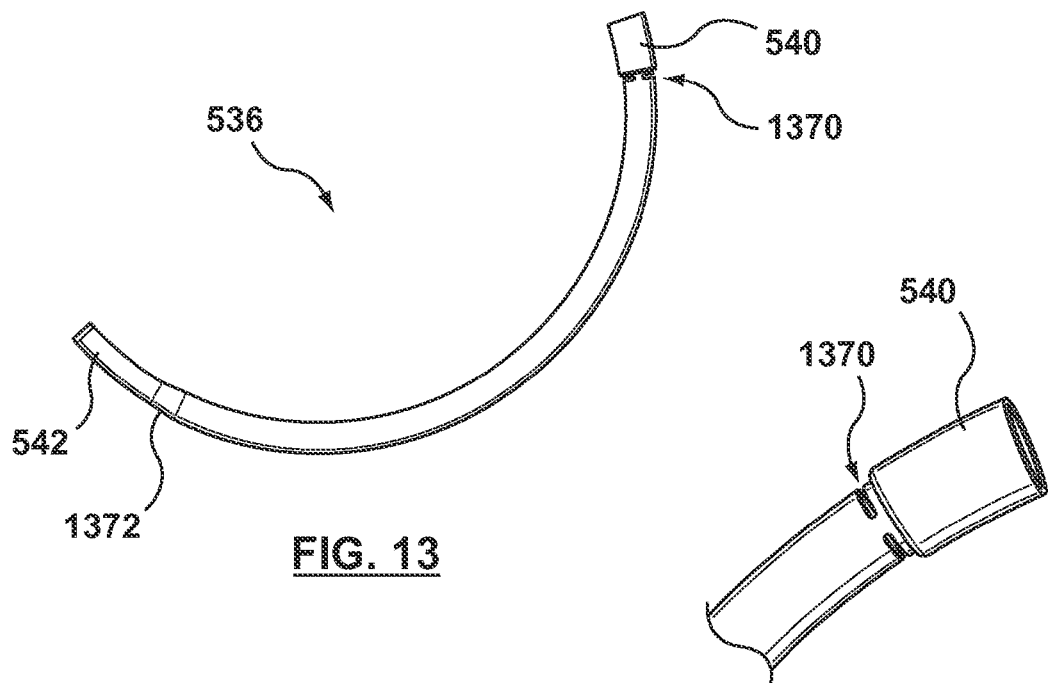
FIG. 13
FIG. 14
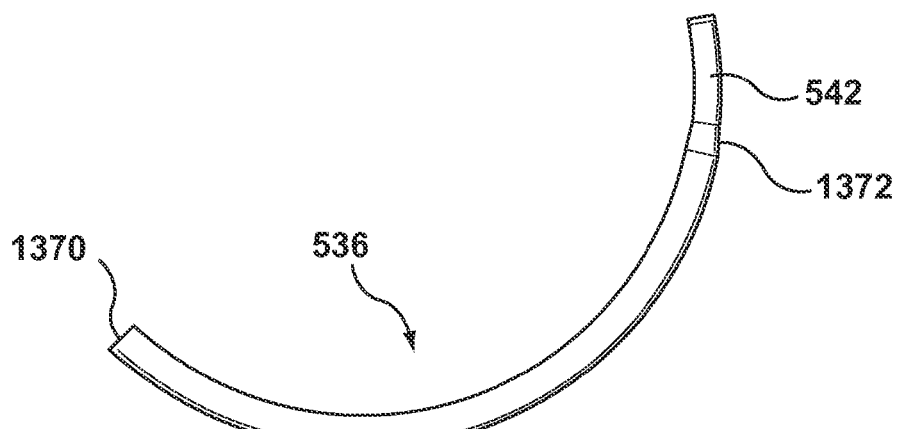
FIG. 15

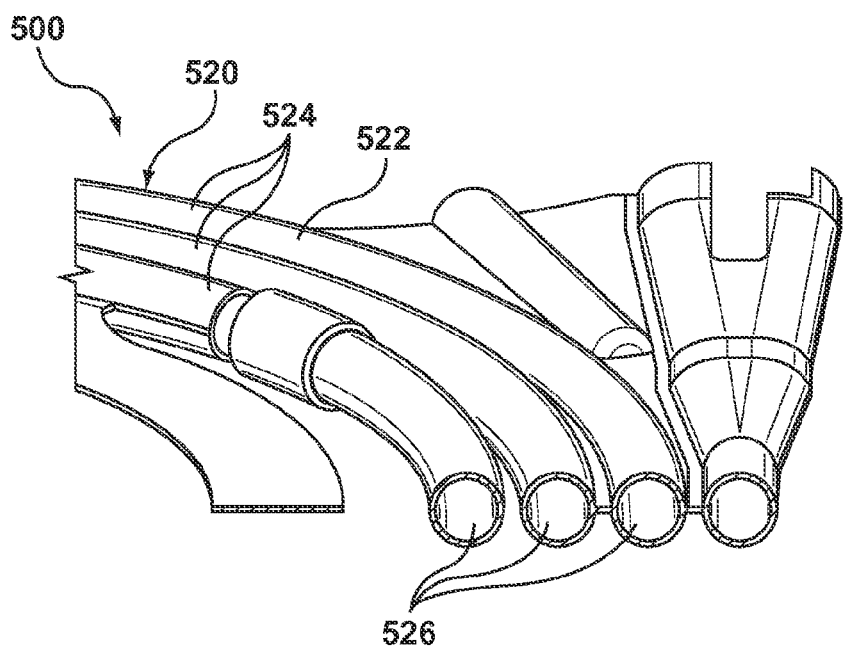
FIG. 18
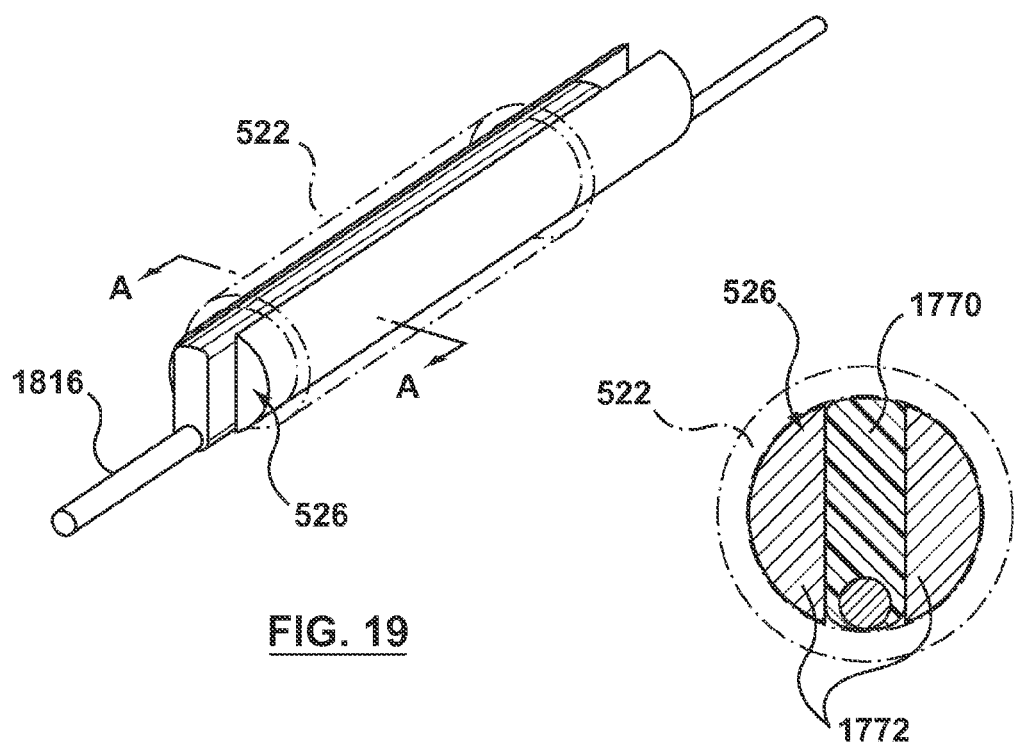
FIG. 19
FIG. 19A

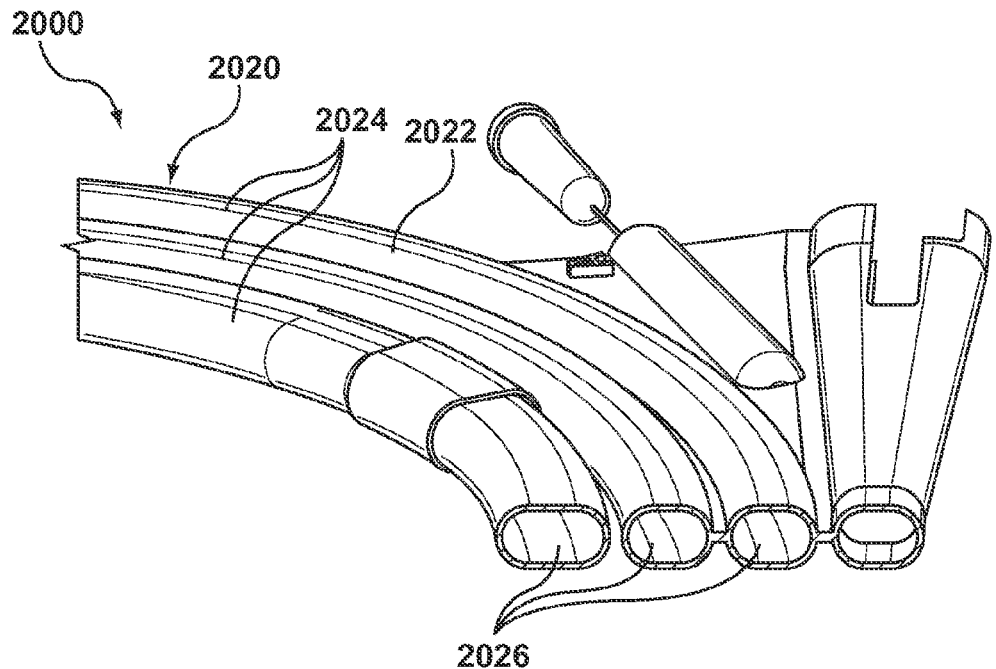
FIG. 20
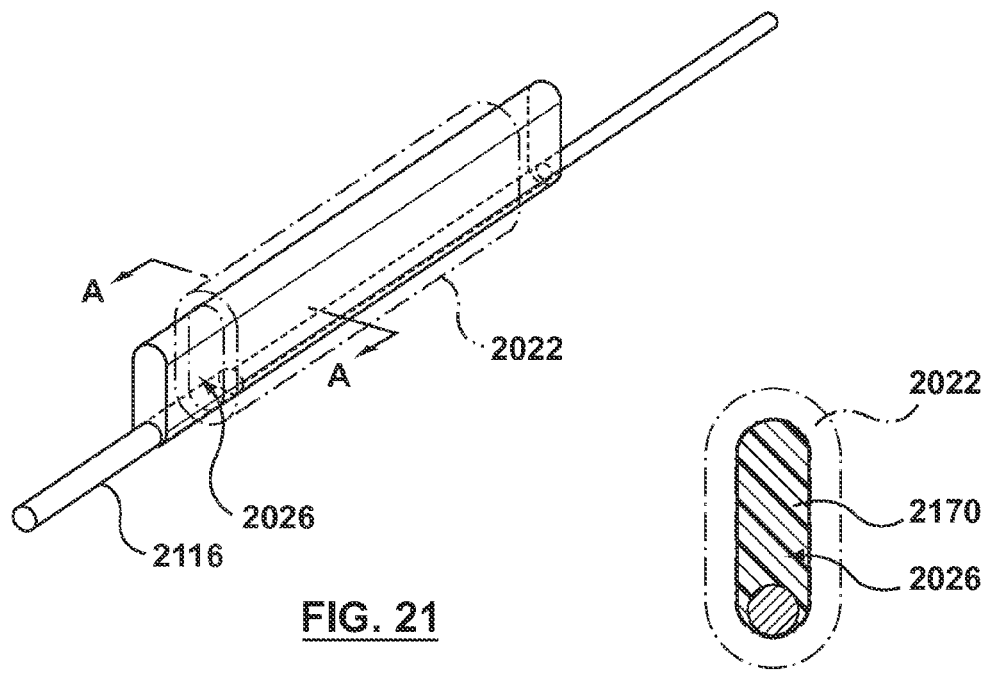
FIG. 21
FIG. 21A

BLOW-MOLDED PACKAGE FOR A CATHETER

FIELD OF THE INVENTION

The present invention relates generally to catheters intended for deployment within a body lumen, such as a patient's vasculature, and more particularly, to packaging for a catheter.

BACKGROUND OF THE INVENTION

Catheters may be inserted into a patient's vasculature and deployed at various locations within the patient for a wide variety of purposes and medical procedures. For example, one type of catheter is used in percutaneous catheter intervention (PCI) for the treatment of a vascular constriction generally known as a stenosis. In this instance, the catheter has a distally mounted balloon that can be placed, in a deflated or unexpanded condition, within the stenosis, and then inflated or expanded to dilate the narrowed lumen of a blood vessel. This type of balloon dilation therapy is generally referred to as percutaneous transluminal angioplasty (PTA). When the treatment is more specifically intended for vessels of the heart, the process is known as percutaneous transluminal coronary angioplasty (PTCA). In other PCI procedures a stent is expanded into contact with the vessel wall to prevent narrowing or restenosis of the artery.

For example, FIGS. 1 and 2 illustrate the deployment of a PTCA treatment catheter 16 within a patient's vasculature. To treat small diameter vessels remote from an entry point into a patient, a guiding catheter 10 may be used to span the distance. Guiding catheter 10 is typically inserted into a large artery 112 near the patient's groin and is then advanced towards the heart H to the entry opening or ostium of a diseased coronary artery. Guiding catheter 10 provides a conduit through which catheters and guidewires, such as treatment catheter 16 and a guidewire 18, can be passed from outside the patient to the vessel being treated. Treatment catheter 16 generally includes a flexible elongated tubular shaft and a luer fitting 14. For certain interventional procedures, treatment catheter 16 may include a dilatation balloon and/or a stent disposed along a distal portion thereof.

Referring now to FIGS. 3-4, catheters are commonly packaged and stored in a packaging hoop 11 as shown in FIG. 3 in accordance with the teachings of the prior art. Packaging hoop 11 consists of a coiled tube 13 having a proximal opening 17 through which treatment catheter 16 is inserted. Several clips 15 are coupled to tube 13 to maintain the tube in the coiled configuration. The overall diameter of packaging hoop 11 is selected to be as small as possible without imparting a lasting curve shape to the generally straight medical device during the shelf life thereof. An overly small diameter hoop 11 may also require excessive friction forces and thereby possibly cause product damage during loading or unloading of the medical device. Luer fitting 14, located at the proximal end of treatment catheter 16, has an area 19 that fits into proximal opening 17 of tube 13, as shown in FIG. 4, in order to secure treatment catheter 16 in packaging hoop 11 until it is removed for clinical use. One potential issue with utilizing clips 15 for holding tube 13 in the coiled configuration is that the packaging may not stay flat because clips 15 cannot grip tube 13 with much force without undesirably pinching or kinking the tubing and thereby restricting the loading and unloading of treatment catheter 16. Furthermore, tube 13 may separate from clips 15 during distribution. In addition, coiled tube 13 is typically formed from an extrusion having a circular cross-section since extruded tubing having a non-circular profile will be predisposed to bend around the profile's major axis. Although non-circular cross-section tubing can be forced to bend around its minor axis to thereby create a hoop 11 having certain advantages such as reduced height, clips 15 cannot constrain coiled tube 13 in this unnatural configuration. Certain catheter device configurations may require the extruded tubing to have an increased diameter and attendant greater stiffness, which may require additional clips 15 to hold tube 13 in the coiled configuration and still has a greater tendency to fall out of plane and not stay flat.

In addition to coiled tube 13 and clips 15, catheter packaging typically includes or requires additional parts or components including a disposable loading tube (not shown) that is necessary to initially load treatment catheter 16 and a finishing tube (not shown) that protects the distal end of catheter 16 during distribution. Various other accessories or components (not shown) may be included in packaging for a catheter, including but not limited to a cannula, a cannula holder, a "looper" or fastener used to clip the catheter in a loop after it is taken out of tube 13, a desiccant and oxygen scavenger, and/or instructions for use that may be associated with the packaging and/or catheter 16. All of the separate components must be assembled together in a cohesive package that is easy to handle and use by operating room personnel.

Accordingly, there remains a need in the art for improved packaging that overcomes these and other disadvantages of currently available catheter packaging.

BRIEF SUMMARY OF THE INVENTION

Embodiments hereof relate to a package for holding a medical device that includes an elongated shaft. The package includes a blow-molded one-piece body that defines a spiral lumen configured to receive the elongated shaft of the medical device. The one-piece body has webbing, an upper spiral rib raised in a first direction relative to the webbing, and a second spiral rib raised in a second opposing direction relative to the webbing. The upper and lower spiral ribs cooperatively form a spiral casing within which the spiral lumen is defined and webbing is disposed between adjacent curved portions of the spiral casing.

Another embodiment hereof relates to a package fir holding a medical device that includes an elongated shaft and a proximal luer fitting. The package includes a one-piece body that includes a spiral casing formed thereon, the spiral casing defining a spiral lumen configured to receive the elongated shaft of the medical device. Webbing is disposed between adjacent curved portions of the spiral casing. A luer retainer is disposed at a first end of the spiral casing, the luer retainer defining an opening configured to receive the proximal luer fitting of the medical device. A loading tube is disposed at a second end of the spiral casing, the loading tube defining a lumen configured to receive a distal end portion of the medical device. The lumen of the loading tube is in fluid communication with the spiral lumen.

Another embodiment hereof relates to a method of blow-molding a package for a medical device having an elongated shaft and a proximal luer. A parison of material is positioned into a mold, and the parison of material is blow-molded to form a one-piece body. The one-piece body defines a spiral lumen configured to receive the elongated shaft of the medical device. The one-piece body has webbing, an upper spiral rib raised in a first direction relative to the webbing, and a second spiral rib raised in a second opposing direction relative to the webbing. The upper and lower spiral ribs collectively form a spiral casing within which the spiral lumen is defined and webbing is disposed between adjacent curved portions of the spiral casing.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 11-16 illustrate a method of using a removable reversible loading tube of the package of FIG. 5.

FIG. 18 is a perspective view of a portion of the package of FIG. 5, wherein a spiral lumen of a spiral casing of the one-piece body has a circular cross-section.

FIG. 19 is a perspective view of a portion of the spiral casing of FIG. 18 with an elongated shaft of a medical device shown positioned therethrough.

FIG. 19A is a cross-sectional view taken along line A-A of FIG. 19.

FIG. 20 is a perspective view of a portion of a package according to another embodiment of the present invention, wherein a one-piece body of the package is formed by blow-molding and wherein a spiral lumen of a spiral casing of the one-piece body has a non-circular cross-section.

FIG. 21 is a perspective view of a portion of the spiral casing of FIG. 20 with an elongated shaft of a medical device shown positioned therethrough.

FIG. 21A is a cross-sectional view taken along line A-A of FIG. 21.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Embodiments hereof relate to a package for a catheter, or more generally, for a package for a medical device having an elongated shaft. The package includes a one-piece or single body that eliminates the need to separately produce and subsequently assemble multiple components thereof. More particularly, prior art catheter packaging included various components or pieces, such as a coiled tube, retaining clips, a cannula holder, a loading tube, a finishing tube, and a looper, that were separately produced and subsequently assembled together. Embodiments hereof relate to a package that has a one-piece body formed by blow-molding to integrally include all of these components and/or to eliminate the need for one or more of these components, thereby reducing the number of separate components or pieces used for packaging a catheter. Although embodiments herein are primarily described for receiving a catheter that has an elongated tubular shaft and a proximal luer fitting, such packages may be used or modified to receive any type of medical device having an elongated shaft, such as but not limited to a guidewire, a sheath, an endoscope, or a microcatheter. The elongated shaft of the target medical device may define a lumen there-through or may be solid, with various cross-sectional sizes or shapes, and the target medical device may or may not include a proximal luer fitting. Further, when embodiments herein are utilized for receiving a catheter, the catheter may be any type of catheter and may or may not include a treatment element, e.g., a deflated balloon or compressed stent, at a distal end portion thereof. For example, embodiments hereof may be utilized to receive a diagnostic catheter or a guiding catheter, in addition to an interventional catheter having a treatment element at distal end portion thereof.

Figure 5:
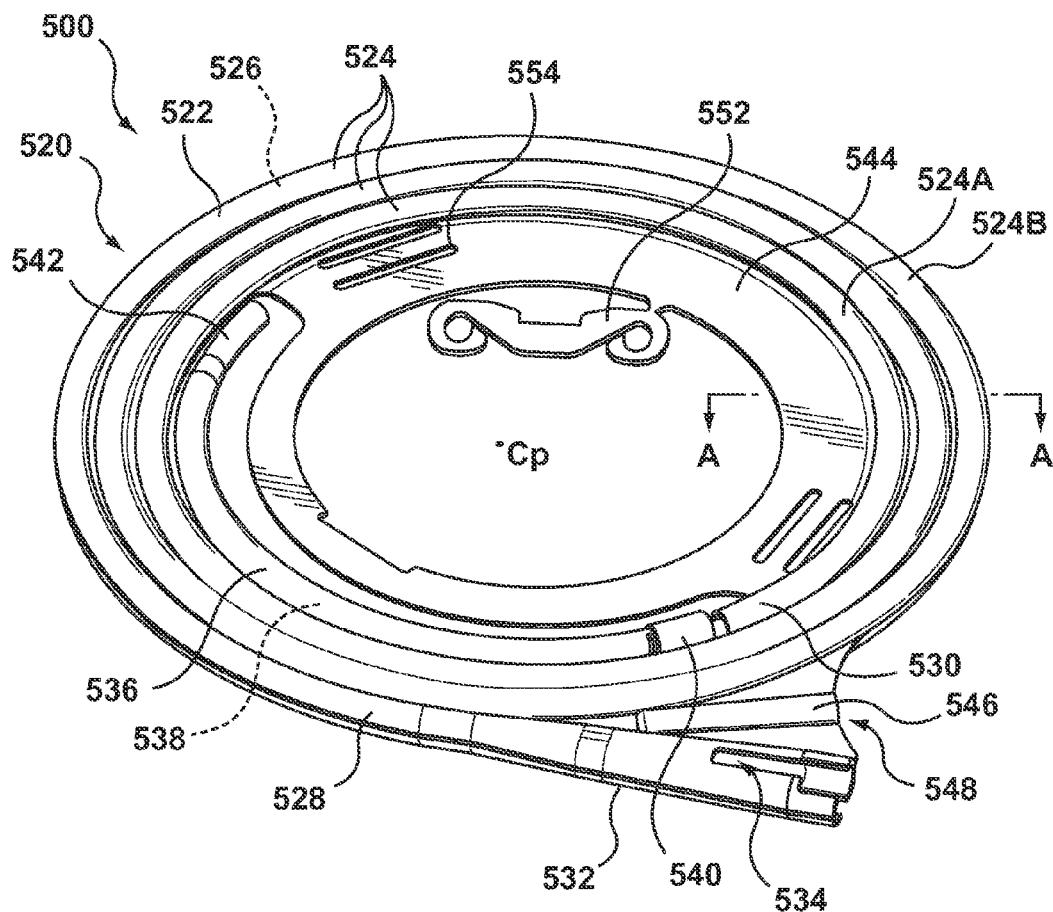
FIG. 5 is a perspective view of a package according to an embodiment of the present invention, wherein a one-piece body of the package is formed by blow-molding.
Figure 6:
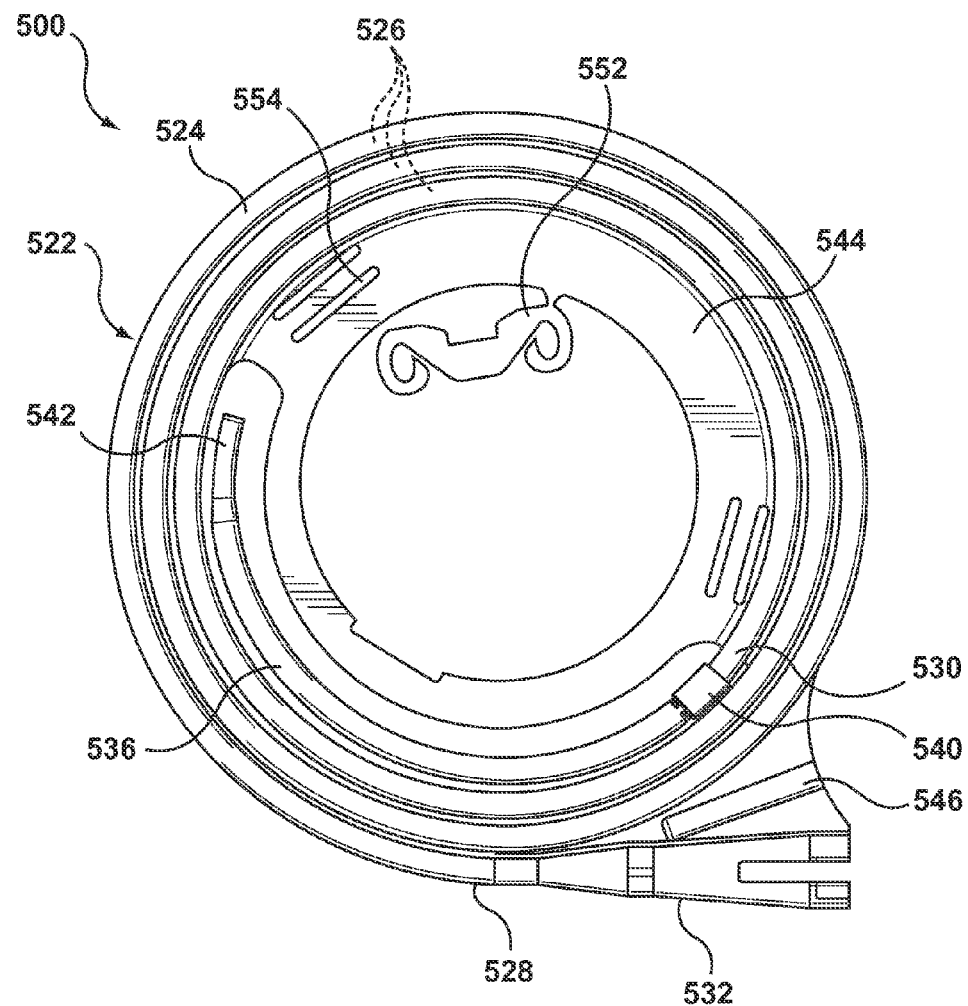
FIG. 6 is a top view of the package FIG. 5.
Figure 7:
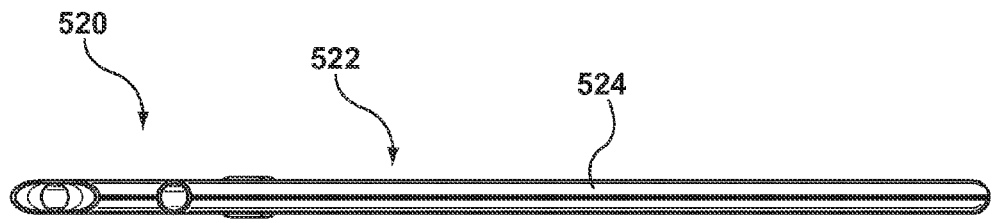
FIG. 7 is a side view of the package of FIG. 5.
Figure 8:
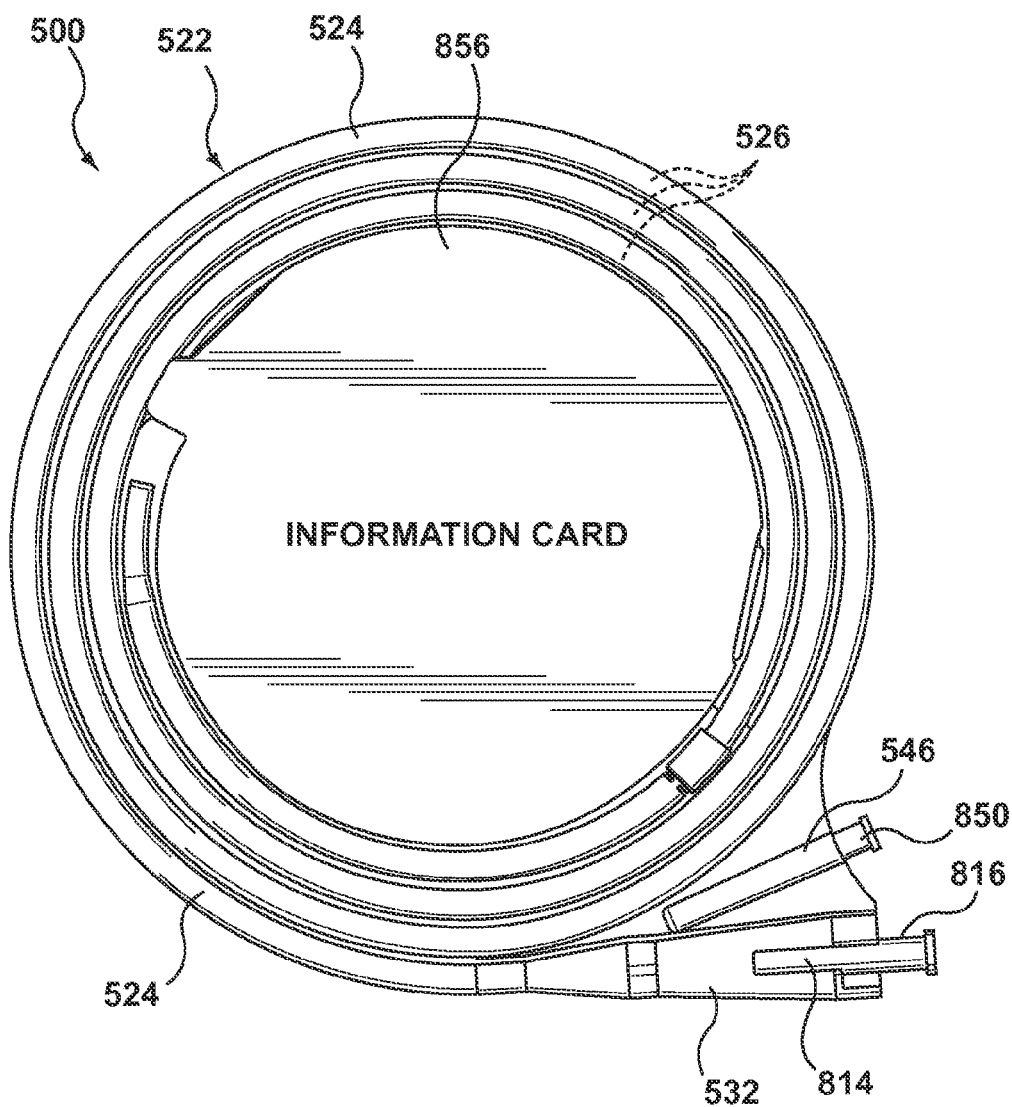
FIG. 8 is a top view of the package of FIG. 5, wherein an information card is shown attached to the one-piece body and a catheter is shown positioned within the one-piece body.

More particularly, with reference to FIGS. 5-8, a package or dispenser 500 includes a one-piece body 520 that is a single or unitary component formed by blow-molding as will be described in more detail herein. FIGS. 5-7 illustrate perspective, top, and side views, respectively, of package 500 without a catheter secured therein, while FIG. 8 illustrates a top view of package 500 with a treatment catheter 816 and a cannula 850 fully secured therein and an information card 856 secured thereto. Blow-molded one-piece body 520 defines a spiral passageway or lumen 526 configured to receive an elongated shaft of a medical device or catheter to protect the medical device from undesired movement and potential damage during transport and storage. More particularly, as best shown in the cross-sectional view of FIG. 5A, one-piece body 520 includes webbing 544 and a first or upper spiral rib or sidewall 521 and a second or lower spiral rib or sidewall 523. Upper and lower spiral ribs 521, 523 are raised or extend in opposing directions with respect to webbing 544 to collectively form a spiral casing 522 within which spiral lumen 526 is defined. One-piece body 520 has an overall annular or ring-shaped molded form or profile, with webbing 544 being substantially flat or planar and spiral ribs 521, 523 forming raised upper and lower surfaces of one-piece body 520. Thus, the general mathematical form of one-piece body 520 comprises the outer turns of a planar or Archimedean spiral curve. In addition to spiral casing 522 and webbing 544, one-piece body 520 also includes a luer retainer 532, a loading tube 536, a cannula holder 546, a looper or fastener 552, and a plurality of slots 554 for attaching an information card thereto. Although separately described herein, spiral casing 522, luer retainer 532, loading tube 536, cannula holder 546, and fastener 552 are integrally formed with webbing 544 to thereby comprise one-piece body 520. Generally, webbing 544 refers to the material of one-piece body 520 that extends between and/or interconnects the other structures of the one-piece body, i.e., spiral casing 522, luer retainer 532, loading tube 536, cannula holder 546, and fastener 552. One-piece body 520 of package 500 may be fabricated from any suitable material that can be blow-molded, for example polypropylene, polyethylene, a nylon/polyethylene blend, polytetrafluoroethylene (PTFE), or any combination thereof.

Figure 25:
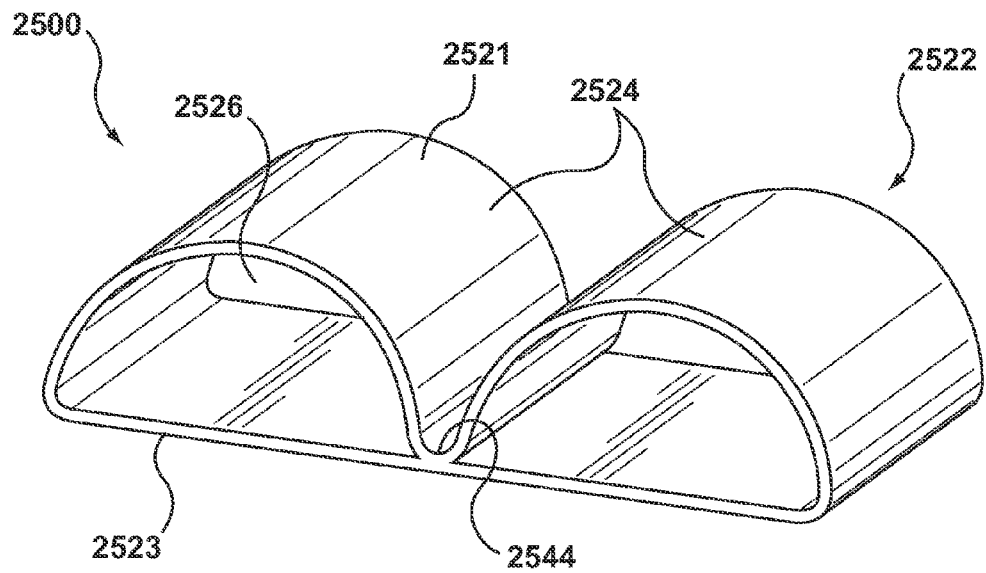
FIG. 25 is a perspective view of a portion of a package according to another embodiment of the present invention, wherein a spiral casing of the package includes asymmetric spiral ribs.

Spiral casing 522, as described above, is formed by upper and lower spiral ribs 521, 523 that are raised or extended in opposing directions from webbing 544. In this embodiment, upper and lower spiral ribs 521, 52.3 each have a semi-circular cross-section such that spiral lumen 526 has a circular cross-section, although the opposing upper and lower spiral ribs may have other configurations so that the spiral lumen may be configured to have non-circular cross-sectional shapes as described in more detail herein. In addition, it is not required that upper and lower spiral ribs 521, 523 have the same configuration. Although spiral casing 522 is shown with symmetric upper and lower spiral ribs 521, 523, the spiral casing formed via blow-molding as described herein may have asymmetric upper and lower spiral ribs according to other embodiments hereof. For example, FIG. 25 shows a schematic illustration of a portion of package 2500 having a spiral casing 2522 with asymmetric upper and lower spiral ribs 2521, 2523. Upper spiral rib 2521 has a semi-circular cross-section while lower spiral rib 2523 is substantially flat or planar. Spiral lumen 2526, which is collectively defined by ribs 2521, 2523, thus has a semi-circular cross-section. Other asymmetric rib configurations are also possible.

Figure 26:
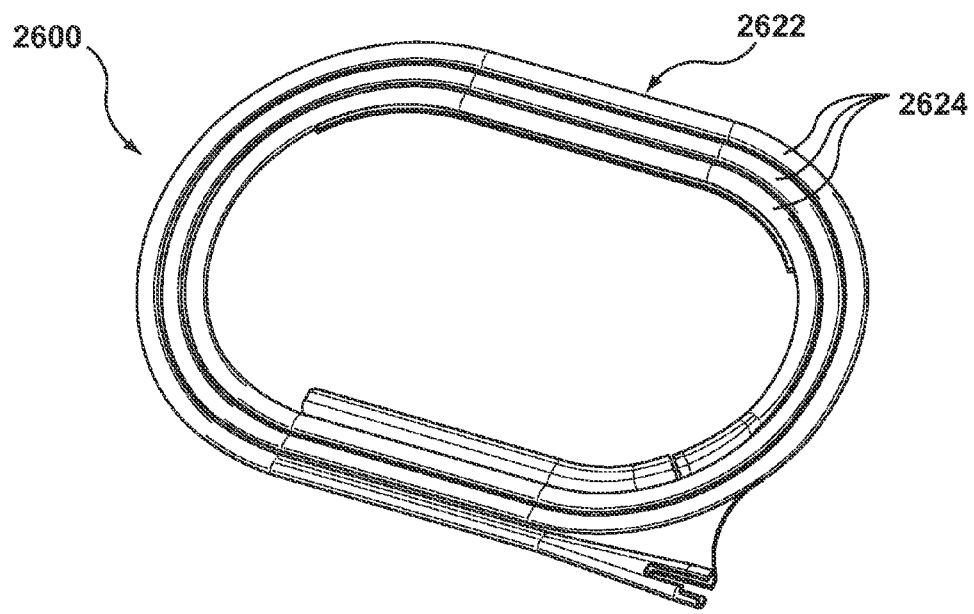
FIG. 26 is a perspective view of a package according to another embodiment of the present invention, wherein the package has an overall oval or "racetrack" configuration.

Spiral casing 522 has a first end 528 and a second end 530. Spiral casing 522 includes a plurality of turns or curved portions 524 that are formed to spiral around a virtual center point $C_p$ of package 500. Although spiral casing 522 has an overall annular or ring-shaped molded form or profile, with curved portions 524 forming circles around center point $C_p$ of package 500, packages formed via blow-molding as described herein may have different forms or profiles according to other embodiments hereof. For example, as shown in FIG. 26, a package 2600 having a "racetrack" or oval molded form or profile is shown. In the so-called "racetrack" shape, casing 2622 has a generally spiral-shaped hoop modified to have opposing side portions that are straight and parallel, and which are joined at their ends by a plurality of curved portions 2624 to form one or more continuous lumens, similar to the casings of packages 500, 1700, 2000 and 2200. The advantage of this configuration is that selected, e.g. distal or proximal, portions of the medical device can be stored in a region of casing 2622 that is completely straight, avoiding the potential for those portions of the device to take a curved set.

Figure 5A:
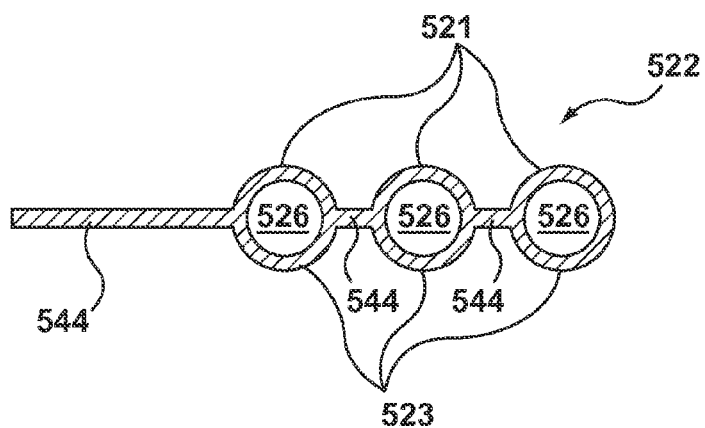
FIG. 5A is a cross-sectional view taken along line A-A of FIG. 5.

As best shown in FIGS. 5 and 5A, radially adjacent curved portions 524, formed by upper and lower spiral ribs 521, 523 of spiral casing 522, are formed slightly spaced apart with webbing 544 extending therebetween. Stated another way, webbing 544 forms a bridging structure between adjacent curved portions 524. In this embodiment, webbing 544 is substantially flat or planar and the plurality of curved portions 524 of spiral casing 522 extend on a single or common plane, as best shown in the side view of FIG. 7, with radii of adjacent curved portions 524 increasing from an innermost curved portion 524A to an outermost curved portion 5249. However, the webbing may alternatively be curved or non-planar as shown in the embodiment of FIG. 25, in which webbing 2544 extends between radially adjacent curved portions 2524 of spiral casing 2522 and is curved or non-planar. In addition, different lengths of elongate medical devices to be housed within package 500 may be accommodated by varying the overall diameter and/or turns of spiral casing 522 to adjust the length of lumen 526, thereby. Further, in another embodiment hereof (not shown), the plurality of curved portions of the spiral casing may extend on more than a single plane. Depending upon application, it may be desirable for the portions of the spiral casing to bend or twist into more than one plane.

Luer retainer 532 is disposed or positioned on package 500 to be at first end 528 of spiral casing 522. Luer retainer 532 defines an opening or lumen 534 that is in fluid communication with spiral lumen 526. Luer retainer 532 is configured to receive a proximal luer fitting of a medical device or catheter. For example, as shown in FIG. 8, a proximal luer fitting 814 of a catheter 816 is shown secured within opening 534 of luer retainer 532. When luer fitting 814 of catheter 816 is secured within luer retainer 532 of package 500, catheter 816 is protected from undesired movement and potential damage during transport and storage. Although catheter 816 includes luer fitting 814, it will be understood by those of ordinary skill in the art that package 500 may be modified to receive a catheter or other medical device having an elongated shaft that does not include a proximal luer fitting.

Loading tube 536 is disposed or positioned at second end 530 of spiral casing 522. Loading tube 536 has a tubular or sleeve-like structure that defines a lumen 538, indicated in phantom in FIG. 5, and which is in fluid communication with spiral lumen 526. Loading tube 536 is configured to receive a distal end portion, e.g., a deflated balloon or compressed stent, of a medical device or catheter. As will be described in greater detail herein with respect to FIGS. 11-16, in an embodiment hereof, loading tube 536 according to an embodiment hereof is integrally formed to be removable and reversible in order to eliminate the need for a separate finishing tube. Reversible loading tube 536 serves to protect the distal end portion of the catheter from undesired movement and potential damage during transport and storage. Although package 500 is described herein with loading tube 536, it will be understood by those of ordinary skill in the art that package 500 may be modified to receive a catheter or other medical device having an elongated shaft that does not include a distal end portion that requires loading tube 536.

As illustrated in FIG. 6, one-piece body 520 includes cannula holder 546 defining an opening 548 configured to receive a cannula for use with a catheter, such as cannula 850 shown in FIG. 8, and a fastener 552 used to clip the catheter in a coiled configuration after it is taken out of package 500 to prevent the catheter from becoming tangled during use. In addition, one or more cuts, slits, or slots 554 may be formed through the material of webbing 544 in order to attach an information card, such as information card 856 shown in FIG. 8, to package 500. More particularly, information card 856 may include one or more integral tabs (not shown) that extend through slots 554 to couple the information card to one-piece body 520. The information card may include any information pertinent to the identification, transport, storage, or use of package 500 and/or the medical device secured therein. In the embodiment depicted in FIGS. 5-7, package 500 includes five slots 554 for attaching an information card but it will be understood by those of ordinary skill in the art that package 500 may be formed with any number of slots. In an alternative embodiment (not shown), the tab-and-slot arrangement may be reversed such that one or more protrusions (e.g. mushroom-shapes, raised buttons, etc.) may be formed on webbing 544, and information card 856 may have one or more openings sized and shaped to engage and lock onto the protrusion(s).

Figure 1:
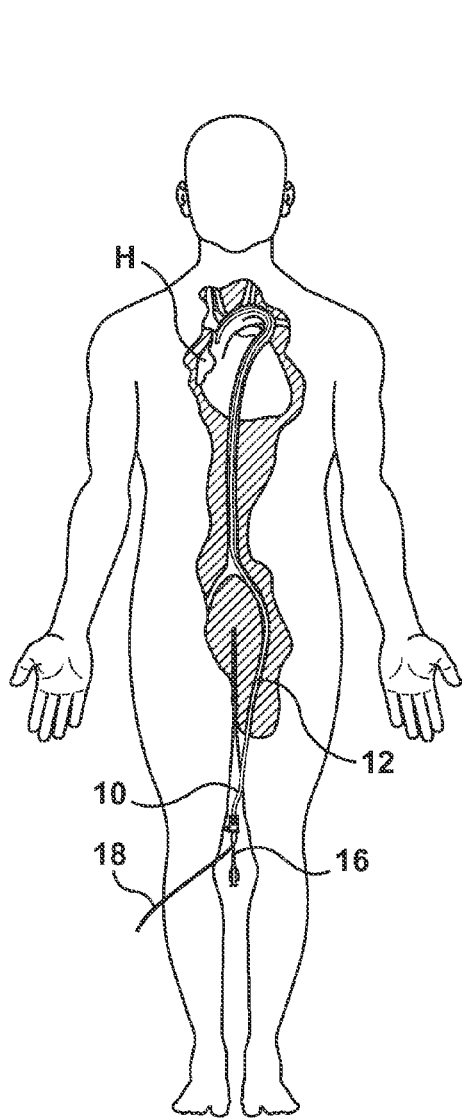
FIG. 1 is a diagrammatic illustration of the deployment of a treatment catheter within a patient's vasculature.
Figure 2:
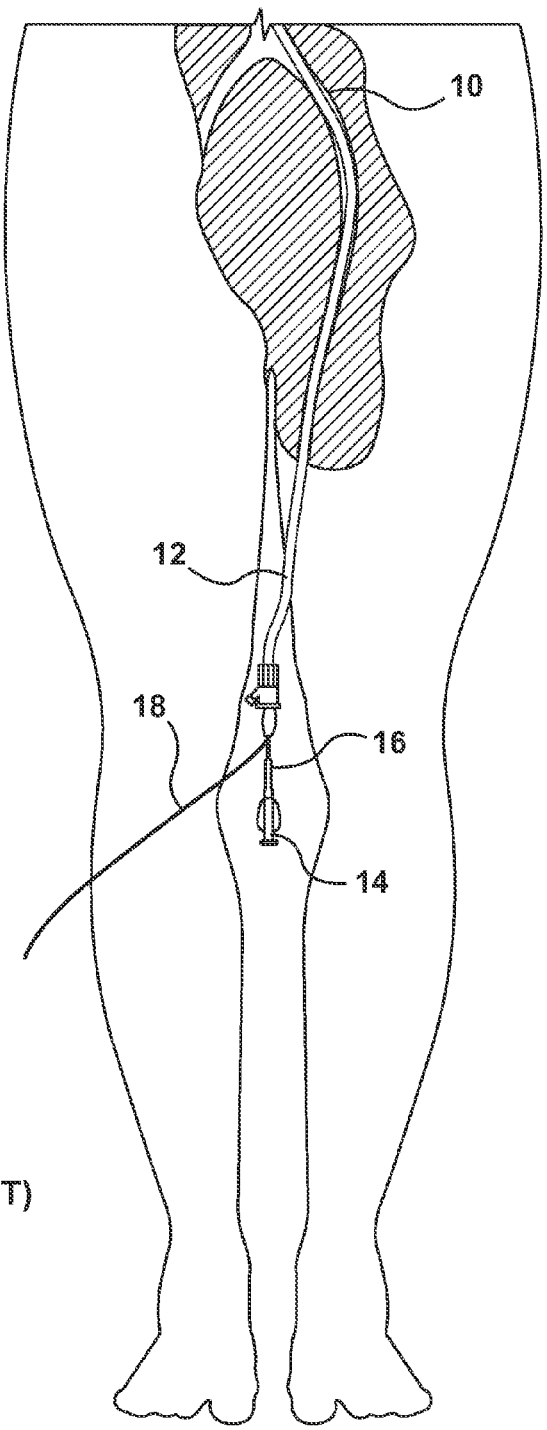
FIG. 2 is an enlarged view of a lower portion of FIG. 1.
Figures 3, 4:
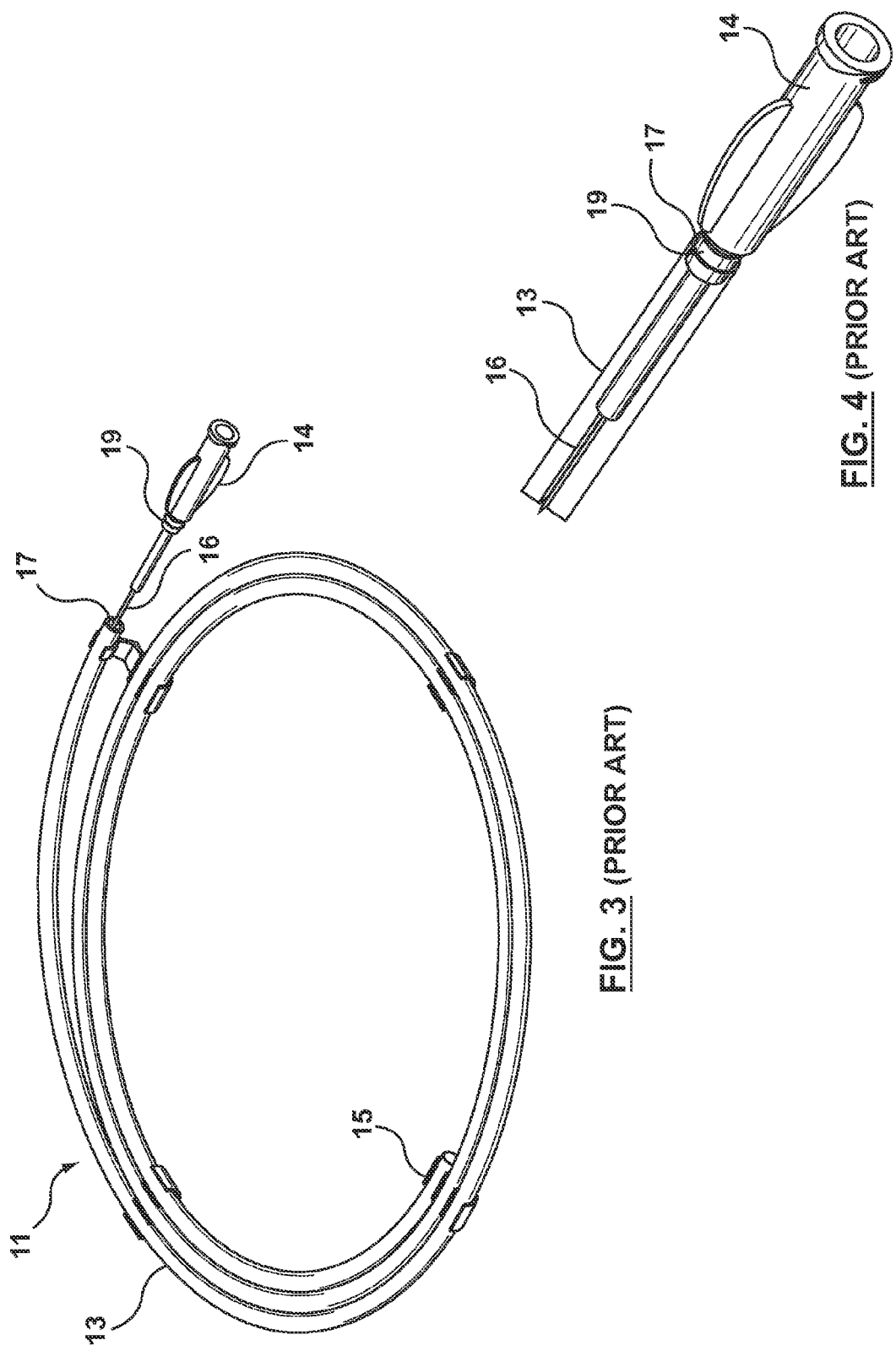
FIG. 3 is a perspective view of a conventional catheter packaging hoop with a catheter partially inserted into the hoop.
FIG. 4 is an enlarged view of a portion of the conventional catheter packaging hoop of FIG. 3 with the catheter fully inserted into the hoop.

By forming package 500 by blow-molding, one-piece body 520 thereof integrally includes spiral casing 522, luer retainer 532, loading tube 536, cannula holder 546, and fastener 552 to provide a reduction in part count and overall cost. Package 500 is also advantageously formed as a rigid one-piece component that lays flat for easy shipment and storage thereof, since adjacent curved portions 524 of spiral casing 522 extend on a common single plane and webbing 544 is integrally formed therebetween to interconnect the adjacent curved portions. Further, with adjacent curved portions 524 integrally formed as joined together via at least a portion of webbing 544, the need for retaining clips, such as those shown in FIG. 1, are not required to hold windings of coiled tubing together.

The method of manufacturing or blow-molding package 500 will now be described in more detail with respect to FIGS. 9-10. Blow molding is a manufacturing process by which hollow thermoplastic parts are formed. In advance of being introduced into a blow molding process, a parison or preform (not shown) is formed from a polymeric moldable material. The preform may have a tube-like shape with a hole or throat in one end through which compressed air can pass. A split mold having an internal cavity of a desired configuration or shape is closed around the parison. Pressurized air is then supplied to the parison, thereby inflating or pushing the polymeric material outward to conform to or match the shape of the internal cavity of the mold. The pressurized air may have a pressure in the range of 100 psi and 150 psi, and in one embodiment, is approximately 125 psi. The blow-molded component is then allowed to cool and shape set and thereafter the mold is opened and the blow-molded component is removed therefrom.

Figure 9:
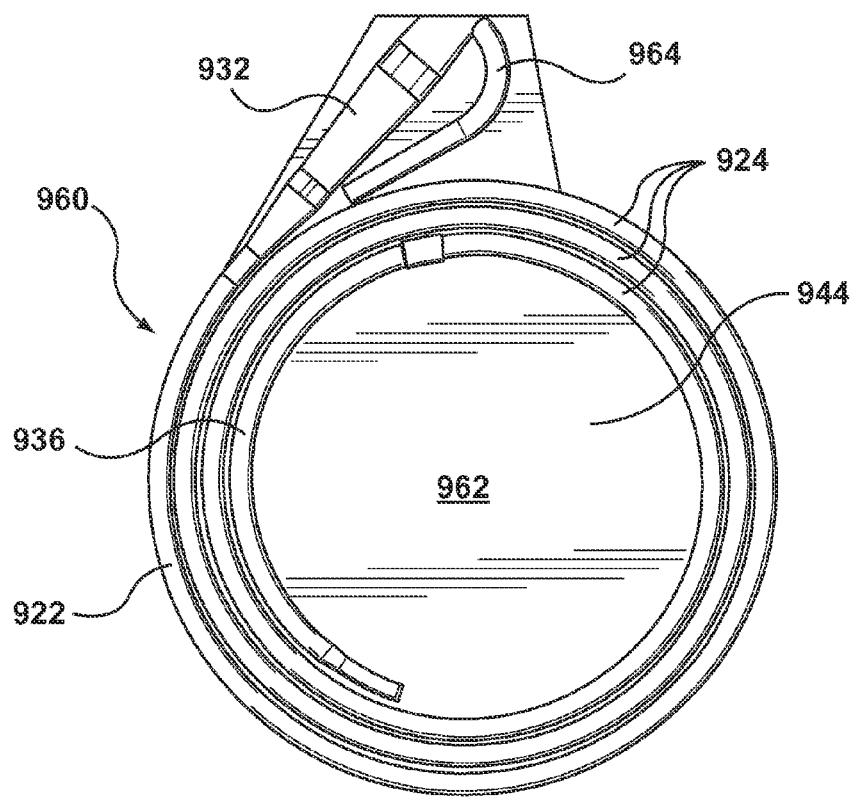
FIGS. 9-10 illustrate a method of manufacturing the package of FIG. 5.

FIG. 9 illustrates a one-piece blow-molded article 960 formed from the above-described blow-molding process. Blow-molded article 960 is similar to one-piece body 520 in that it integrally includes a spiral casing 922 having a plurality of curved portions 924, a luer retainer 932, a loading tube 936, and webbing 944. However, unlike one-piece body 520 of package 500, blow-molded article 960 is unfinished as it does not yet include a formed cannula holder but rather includes an airway or channel 964 which is in fluid communication with the lumen of luer retainer 932. In addition, unlike one-piece body 520 of package 500, webbing 944 forms a full or connected center region 962 within curved portions 924 and does not yet include a formed looper or a plurality of slots. Blow-molded article 960 has an overall circular molded form or shape with the central region 962 of webbing 944 being surrounded by spiral casing 922. In addition, unlike one-piece body 520 of package 500, loading tube 936 of blow-molded article 960 is joined or integrally connected to spiral casing 922 at this stage of manufacture.

Figure 10:
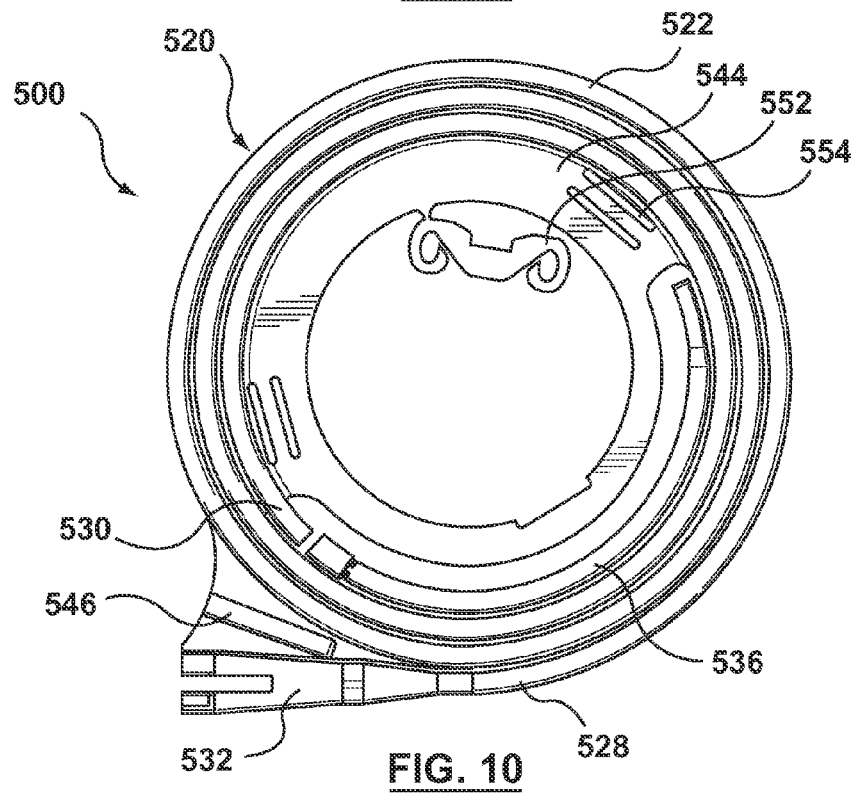
Figure 11:
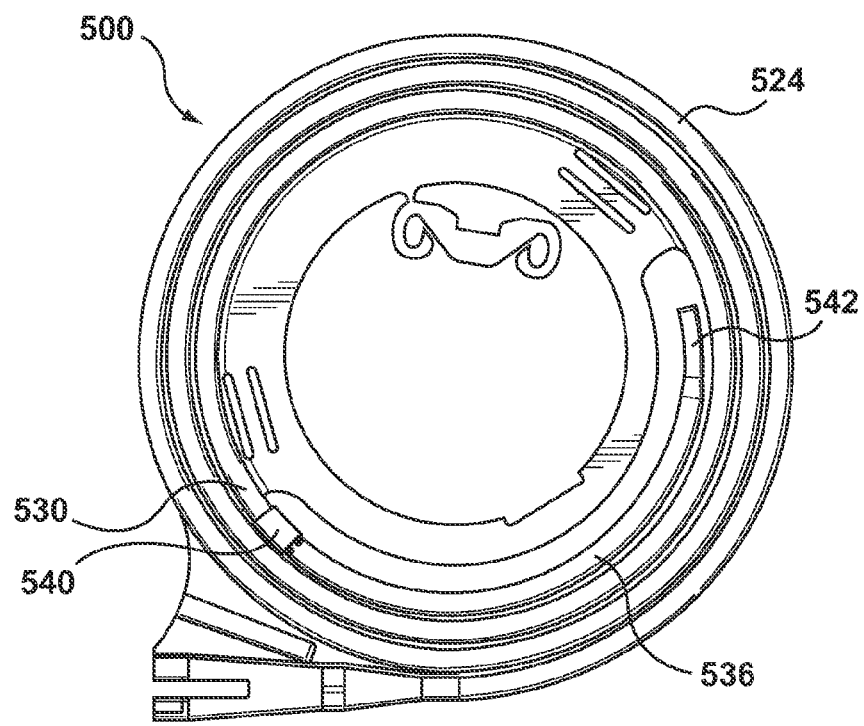
Figure 12:
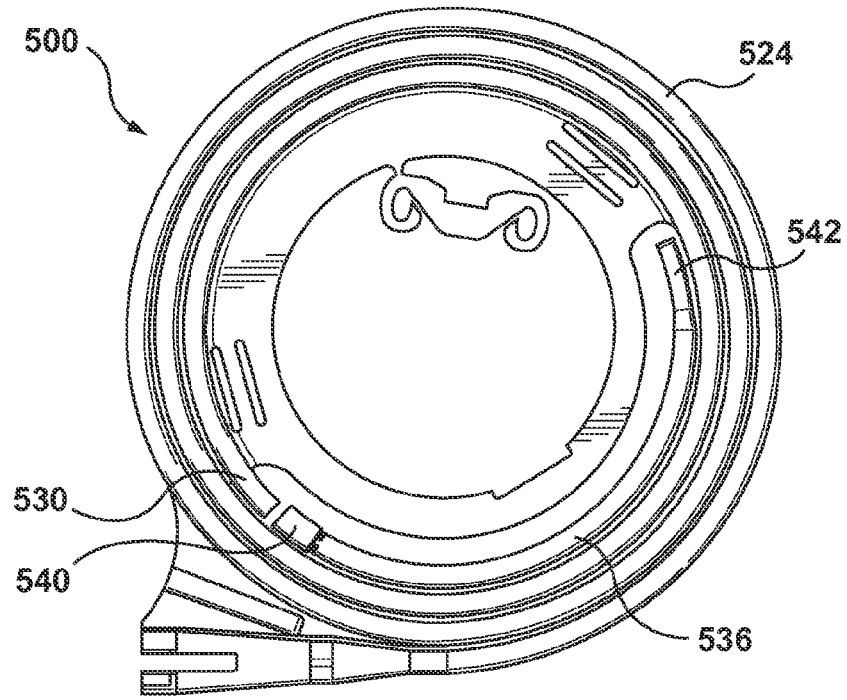

With reference to FIGS. 9 and 10, one or more secondary die cutting steps transform blow-molded article 960 into one-piece body 520 of package 500. More particularly, a die cutting step removes a portion of blow-molded component 960 to disconnect channel 964 from the lumen of luer retainer 932, thereby forming or creating cannula holder 546 and luer retainer 532 of package 500. In addition, a die cutting step selectively removes portions of center region 962 of webbing 944 of blow-molded article 960, as well as other portions of webbing 944, in order to form or create fastener or "looper" 552 and slots 554 for attaching an information card thereto. Furthermore, a die cutting step separates integrally-formed loading tube 936 from spiral casing 922, thereby creating removable reversible loading tube 536 of package 500. Unlike other trimmed-away scrap portions of blow-molded article 960, loading tube 536 has functional utility, as will be described in further detail below. The die cutting steps described herein may be simultaneously performed in a single die cutting step, or may be sequentially performed in a die cutting operation having more than one step. In addition, as would be understood by one of ordinary skill in the art, alternative methods to die cutting may be used to remove material of blow-molded article 960 including but not limited to punching, pinching off, trimming, water jetting, laser cutting, and other methods known in the art for removing or shaping a molded article.

Removable reversible loading tube 536 will now be described in more detail with reference to FIGS. 11-16. In an embodiment hereof, after reversible loading tube 536 is severed from spiral casing 522 as described above with respect to FIGS. 9 and 10, loading tube 536 has a larger first end 540 and a smaller second end 542. See FIG. 13. Larger first end 540 of loading tube 536 has an inner diameter sized and shaped to have a sliding or interference fit over second end 530 of spiral casing 522 in a first configuration shown in FIG. 11. Smaller second end 542 has an outer diameter sized and shaped to have a sliding or interference fit into second end 530 of spiral casing 522 in a second configuration shown in FIG. 16. Reversible loading tube 536 is thus configured to selectively alternate between the first and second configurations.

In the first configuration, a catheter may be loaded through curved portions 524 of spiral casing 522 until a distal end portion of the catheter is positioned within loading tube 536. Since larger first end 540 of loading tube 536 is disposed over spiral casing 522, the balloon of the catheter does not have to cross over the edge of first end 540 of loading tube 536, which could possibly damage the balloon. Loading tube 536 also serves to protect the distal end portion of the catheter after it is loaded into package 500. In the first configuration, reversible loading tube 536 may optionally be removed to permit any secondary operation to be performed on the distal end of the catheter after the catheter is loaded into the package. Such secondary operations may include, but are not limited to, crimping of a stent positioned over the distal end of the catheter or applying a drug coating onto the balloon of the catheter or any post-forming operation for the distal portion of the catheter.

Figure 16:
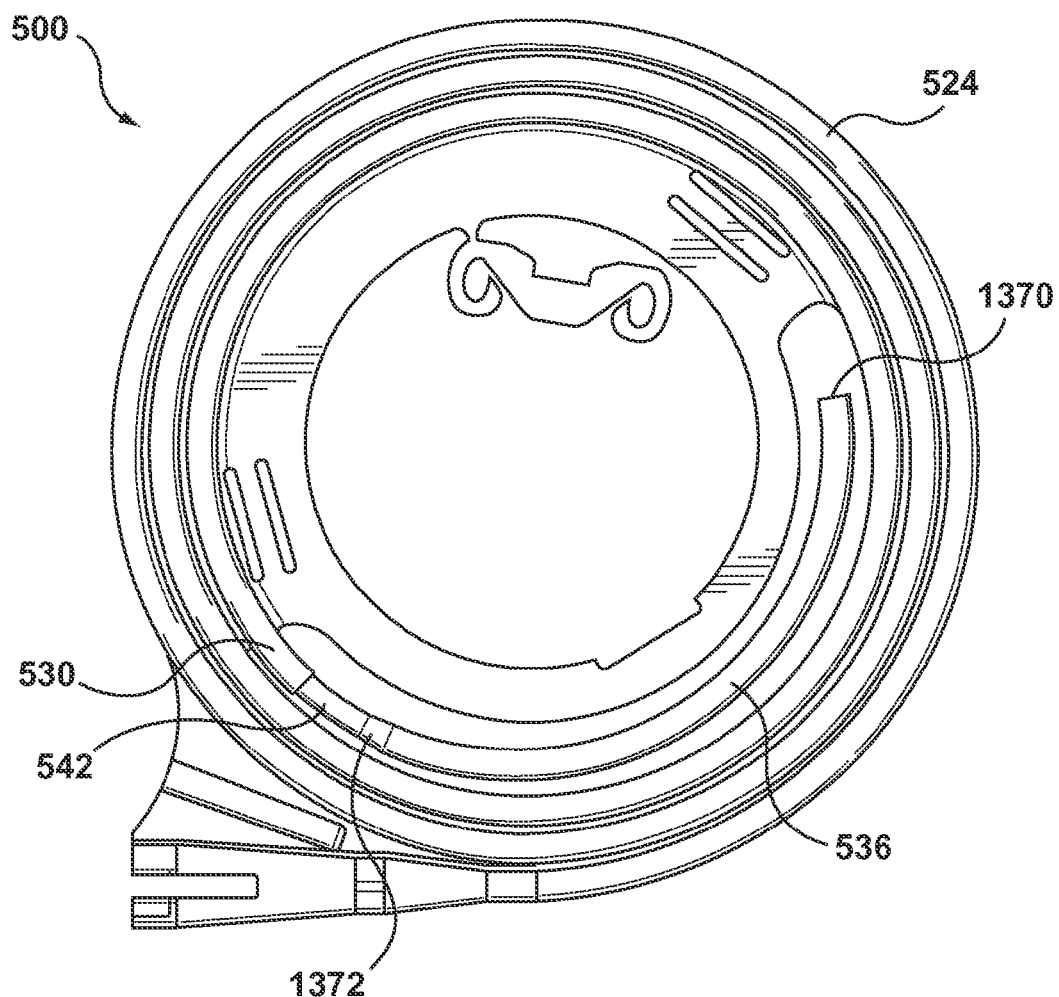

After loading tube 536 is removed, a stent may be positioned over the distal end portion of the catheter and crimped or otherwise compressed into a delivery configuration as understood by one of ordinary skill in the art. Loading tube 536 is then re-positioned over the crimped stent in its reversed, or second configuration in which smaller second end 542 of loading tube 536 is inserted into second end 530 of spiral casing 522 as shown in FIG. 16. Loading tube 536 in its second configuration serves to protect the crimped stent and distal end portion of the catheter during further processing, transport, and storage. In addition, loading tube 536 in its second configuration allows fir a smooth withdrawal of the crimpled stent and distal end portion of the catheter when the catheter is removed from package 500. Since smaller second end 542 of loading tube 536 is positioned within spiral casing 522, the balloon and crimped stent do not cross or drag over the edge of second end 530 of spiral casing 522 when the catheter is removed.

When loading tube 536 is in its second configuration, larger first end 540 of loading tube 536 is no longer needed and can be removed and discarded. As shown in FIGS. 13-14, loading tube 536 may include an area of weakness 1370 such as notches or perforations that allow larger first end 540 to be torn away from the remainder of loading tube 536 for easy removal thereof. FIG. 15 illustrates loading tube 536 after larger first end 540 has been torn away or removed, with larger first end 540 no longer attached to the loading tube. Removing and discarding larger first end 540 minimizes the thickness of package 500.

In another embodiment hereof one or more structures of one-piece body 520 may be formed via over-molding rather than blow-molding. For example, in another embodiment hereof, blow-molded article 960 which is initially formed from a blow-molding process may integrally include a spiral casing, a loading tube, and webbing. The luer retainer and/or the cannula holder may be subsequently over-molded at the outermost end of the spiral casing of the blow-molded article 960. The resulting package having an overmolded liter retainer and/or cannula holder would be similar to package 500 in that all structures of the package would be integrated and thereby form a single or unitary body or package component. However, the process for forming a package having an overmolded luer retainer and/or cannula holder requires an additional molding step. In an embodiment hereof, an over-molded luer retainer and/or cannula holder may be formed with a different material than the blow-molded article. In another embodiment, an overmolded luer retainer and/or cannula holder may be formed with the same material as the blow-molded article but overmolding may be utilized due to the particular shape or configuration of the luer retainer and/or cannula holder.

Alternatively, blow-molded article 960 can be co-molded from a co-extruded parison to provide an advantageous combination of material properties. For example, one material can be stiff and tough, while another material is highly flexible. The co-extruded parison or pre-form can include two or more different thermoplastic materials combined in coaxial layers, in sequential co-extrusion, or in striping extrusion, e.g. side-by-side, arrangements. The material characteristics can serve different packaging requirements within the same hoop. In another example, one material serves as a light barrier for an area of the product that is light sensitive while a clear material allows a barcode on a luer fitting to be scanned.

Figure 17:
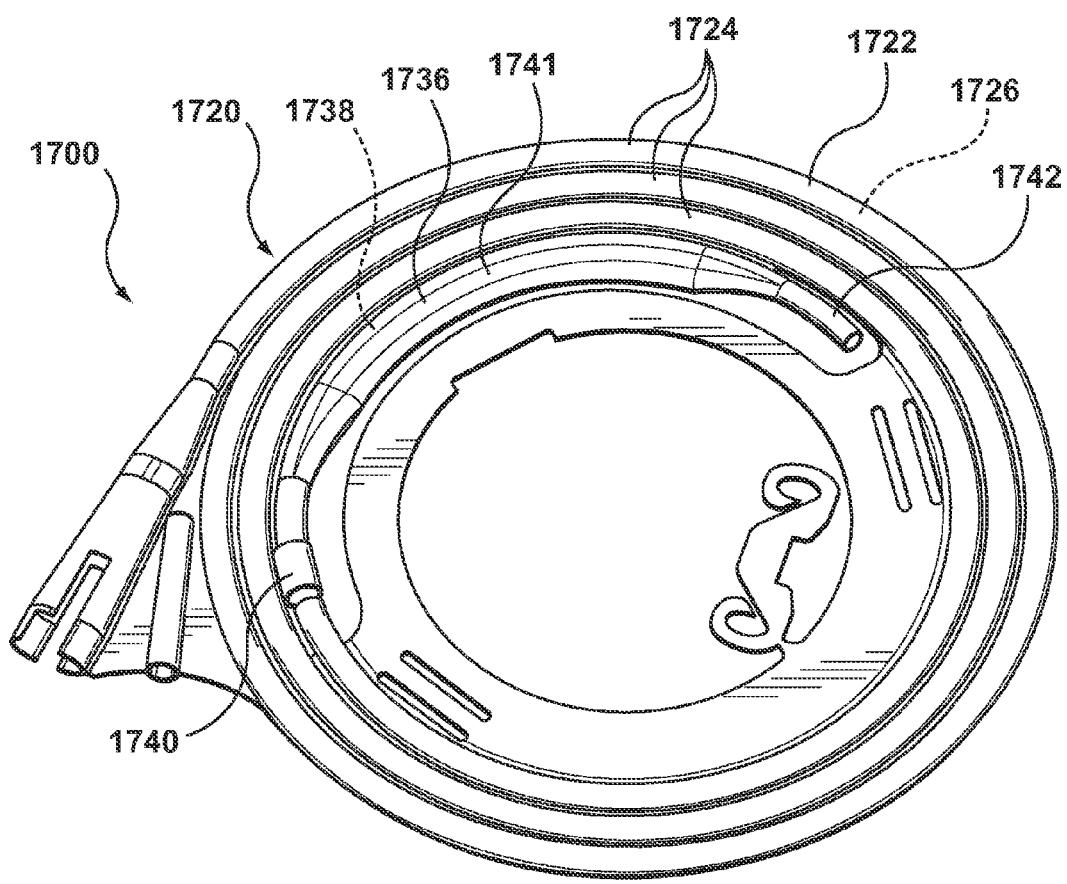
FIG. 17 is a perspective view of a package according to another embodiment of the present invention, wherein a one-piece body of the package is formed by blow-molding and a cross-sectional shape of a lumen of a removable reversible loading tube of the one-piece body varies along the length thereof

In addition to being formed as a single or unitary component, there are several other advantages that result from constructing package 500 via blow-molding. With respect to prior art catheter packaging having a coiled tube formed via extrusion, features and complexity of packaging components significantly impact their manufacture, assembly, cost, time to market, and rigidity. For example, packaging having a coiled tube formed via extrusion result in only a circular cross-section of constant radius. However, complex single piece blow-molded dispensers may be configured and produced without significant cost, overhead, lead time and structural implications. Such design variations may be easily achieved by changing the shape of the mold utilized in the blow-molding process. For example, a blow-molded catheter package may incorporate multiple spiral lumens or pathways for receiving multiple catheters or other elongated medical devices, and may be formed to have non-circular lumens and/or lumens having a size or cross-sectional shape that varies along a length thereof FIG. 17 is a perspective view of a package 1700 according to another embodiment hereof. Package 1700 includes a one-piece body 1720 formed via blow-molding. One-piece body 1720 is similar to one-piece body 520 described above except that one-piece body 1720 includes a loading tube 1736 that has a cross-sectional shape that varies along the length thereof. More particularly, loading tube 1736 has a circular cross-section at first end 1740 and a circular cross-section at second end 1742. However, an intermediate portion 1741 of loading tube 1736 has an oval or oblong rather than circular cross-section in order to better accommodate the distal end portion of the catheter. More particularly, widening the cross-section of the loading tube along an intermediate portion thereof reduces dragging friction on the catheter during loading and removal thereof and also lowers the required insertion force, thereby preventing potential kinking of the catheter during loading. In addition, the wider cross-section of the loading tube along an intermediate portion thereof may permit the distal end of the catheter to straighten out for shelf storage even if the loading tube itself is slightly curved in storage. Alternatively, the distal end of a catheter may at least partially relax to a pre-formed helical shape within intermediate portion 1741 rather than being stored in a constrained, straightened shape. Thus, the shape or profile of a lumen or pathway 1738 defined by loading tube 1736 varies along the length thereof. The transition area between first end 1740 and intermediate portion 1741, as well as the transition area between intermediate portion 1741 and second end 1742, may be formed smooth and tapered. Notably, in addition to varying along its own length, the oval cross-section of intermediate portion 1741 of loading tube 1736 is a different cross-sectional shape from the cross-sectional shape of a spiral lumen 1726 formed by curved portions 1724 of spiral casing 1722, which in this embodiment has a circular cross-section.

In addition to varying the lumen profile of the loading tube, a package having a spiral casing with a non-circular cross-section may be blow-molded in accordance with embodiments hereof. FIGS. 18, 19, and 19A illustrate a portion of package 500. As previously described, curved portions 524 of spiral casing 522 form spiral lumen 526. Spiral lumen 526 has a circular cross-section, as discussed above with respect to FIG. 5A and also shown in the perspective view of FIG. 18. When a catheter 1816 is positioned within circular cross-section of lumen 526 as shown in FIG. 19, passage of catheter 1816 requires only approximately 45% of the total volume of the circular cross-section of lumen 526. Conversely, approximately 55% of the total volume of circular cross-section of lumen 526 is not required to allow catheter 1816 to pass there-through. FIGS. 19 and 19A illustrate a required or necessary region 1770 in the center of lumen 526 and two side unnecessary regions 1772. The unnecessary regions 1772 on each side of circular cross-section of lumen 526 may be eliminated without affecting the performance of catheter 1816 or package 500. In view of the foregoing, FIGS. 20, 21, and 21A illustrate a portion of a package 2000 according to another embodiment hereof. Package 2000 includes a one-piece body 2020 formed via blow-molding. One-piece body 2020 is similar to one-piece body 520 described above except that one-piece body 2020 includes a spiral casing 2022 having a plurality of curved portions 2024 that define a spiral lumen 2026 having a noncircular cross-section, as best shown in the perspective view of FIG. 20. When a catheter 2116 is positioned within the oval or oblong cross-section of lumen 2026 as shown in FIGS. 21 and 21A, passage of catheter 2116 requires substantially all of the total volume of the oval lumen 2026 as indicated by necessary region 2170.

The oblong cross-section of spiral casing 2022 has several advantages including but not limited to material savings, cost savings, size and weight reduction, and increased package stiffness. More particularly, when a stent or balloon coupled to a distal end portion of a catheter passes through a spiral casing, it does not bend, i.e., it remains substantially straight, when passed through curves or bends of the casing. Thus, the cross-section of the casing must have a bend or turn radius which allows passage of a substantially straight stent or balloon. In the case of a spiral casing having a circular cross-section, depending upon the length of the stent or balloon, it may be required to increase the cross-sectional diameter of the casing in order to provide the casing with a sufficient bend or turn radius. Increasing the cross-sectional diameter, however, results in higher material costs as well as increased size and weight of the spiral casing. However, compared to a package or casing having a circular cross-section, the oblong cross-section of spiral casing 2022 can be made wider in the radial direction while having the same dimension in the axial direction. The wider radial dimension of the oblong cross-section of spiral casing 2022 provides the curved portions of the spiral casing with a larger or increased bend or turn radius without requiring the higher material costs, increased size, and increased weight of a casing with a larger circular cross-section. Reducing the size and weight of the package further results in a shipping cost savings and thinner packages allows additional inventory to be stored within the same customer shelf space.

Figure 22:
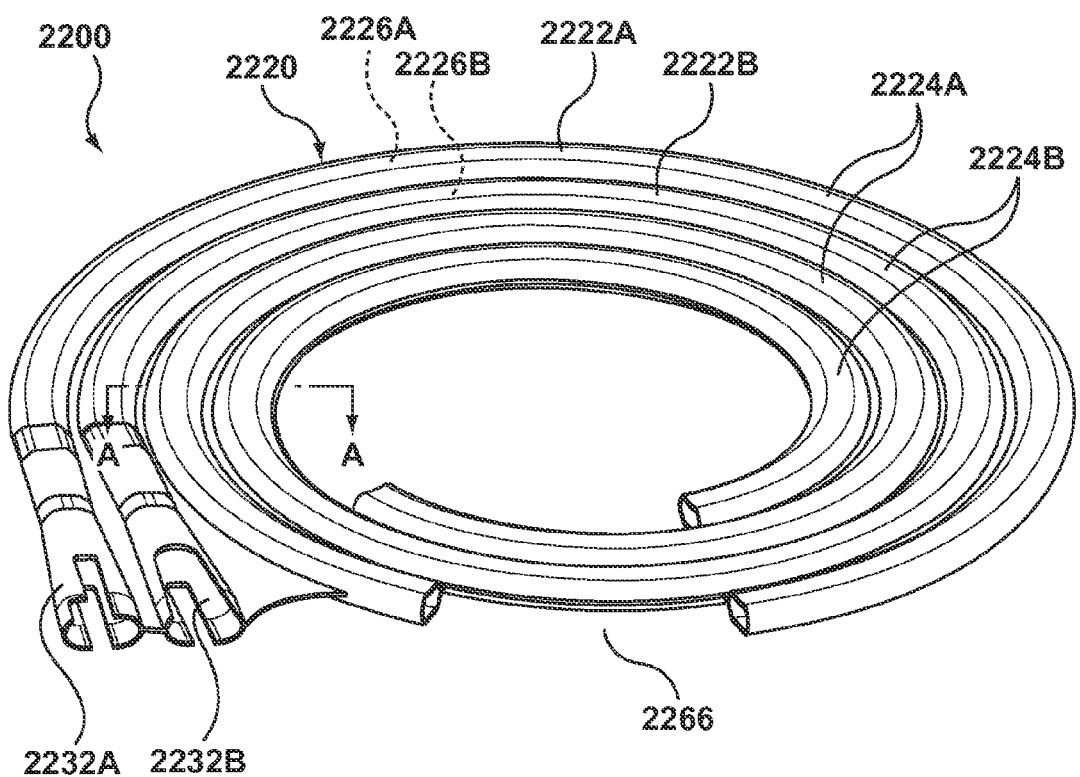
FIG. 22 is a perspective view of a package according to another embodiment of the present invention, wherein a one-piece body of the package is formed by blow-molding and includes two spiral casings that each define a spiral lumen such that the package is configured to receive two medical devices.
Figure 22A:
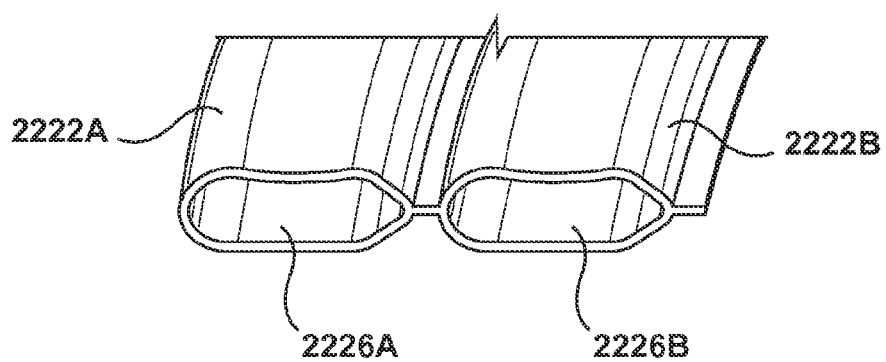
FIG. 22A is a cross-sectional view taken along line A-A of FIG. 22.

In another embodiment, a unitary or single-piece package may be blow-molded with two spiral casings that each define a spiral lumen such that the blow-molded package is configured to receive two catheters or other elongated medical devices, each in their own dedicated lumen. For example, FIGS. 22 and 22A illustrate a package 2200 according to another embodiment hereof. Package 2200 includes a one-piece body 2220 formed via blow-molding. One-piece body 2220 is similar to one-piece body 520 described above except that one-piece body 2220 includes two spiral casings 2222A, 2222B, each spiral casing 2222A, 2222B having a plurality of curved portions 2224A, 2224B that define respective spiral lumen 2226A, 2226B. Curved portions 2224B of spiral casing 2222B are nested within or sandwiched between curved portions 2224A of spiral casing 2222A. In this embodiment, the cross-section of each spiral lumen 2226A, 2226B is oval, as best shown in the cross-sectional view of FIG. 22A. One-piece body 2220 also includes two luer retainers 2232A, 2232B. Accordingly, package 2200 is configured to secure two catheters or other elongated medical devices, each in their own dedicated lumen. Alternatively, the dual spiral lumens of package 2200 may be utilized in other applications such as shipping package 2200 with one of the spiral lumens empty and then being utilized to store and dispense support tools during a procedure.

Package 2200 also includes another feature which may be incorporated into any embodiment described herein. Spiral casing 2222A of package 2200 includes a discontinuous portion 2266. Discontinuous portion 2266 allows a user to access the device stored within the spiral casing to assist loading and/or removal of the device. For example, a guidewire (not shown) or other elongated device not having a proximal luer may be stored within spiral casing 2222A. It may be difficult for a user to remove the guidewire from spiral casing 2222A since the guidewire does not have a proximal luer for the user to grasp. Discontinuous portion 2266 allows a user to grasp the guidewire mid-length and advance it out of spiral casing 2222A.

Figure 23:
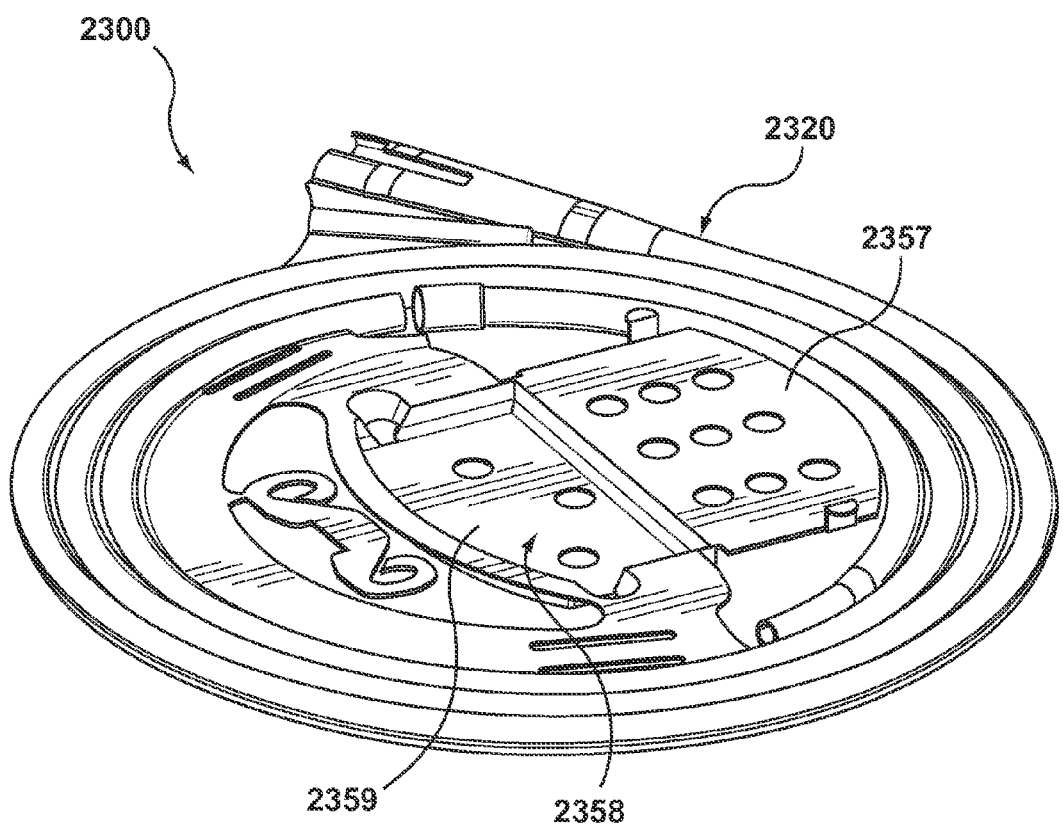
FIG. 23 is a perspective view of a package according to another embodiment of the present invention, wherein a one-piece body of the package is formed by blow-molding and includes an integral compartment.
Figure 24:
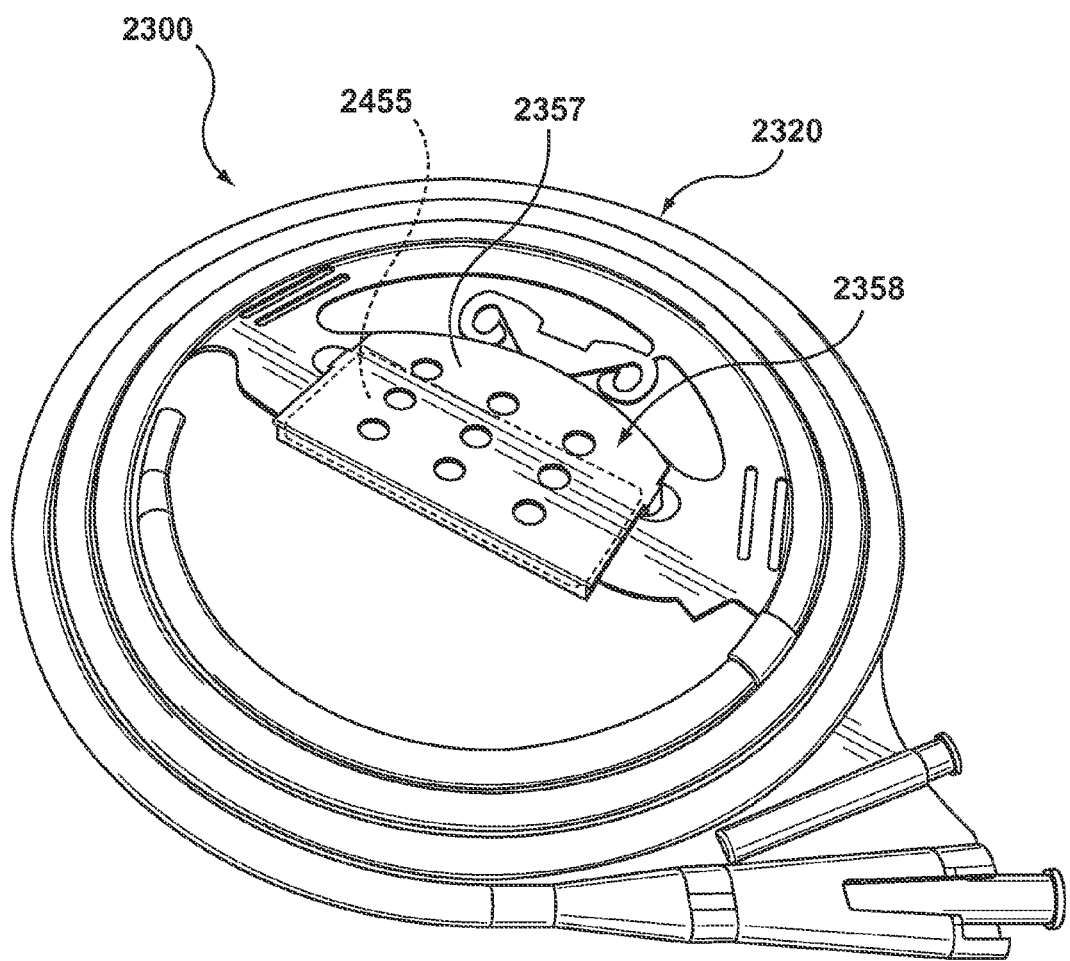
FIG. 24 is a perspective view of the package of FIG. 23, wherein an oxygen scavenger is shown positioned within the integral compartment.

Catheter packages formed via blow-molding may be modified to include various other integrated accessory components by changing the shape of the mold utilized in the blow-molding process. For example, in another embodiment hereof, the catheter package includes a blow molded integral compartment for retaining an oxygen and/or moisture scavenger. FIG. 23 illustrates a perspective view of a package 2300 as formed without an oxygen scavenger secured therein, while FIG. 24 illustrates a perspective view of package 2300 with an oxygen scavenger 2455 fully secured within a compartment 2358 thereof. Package 2300 includes a one-piece body 2320 formed via blow-molding that is similar to one-piece body 520 described above except that one-piece body 2320 includes an integral compartment 2358 for retaining the oxygen and/or moisture scavenger 2455. As shown in FIGS. 23 and 24, a first portion or half 2357 of compartment 2358 is configured to fold over the remaining second portion or half 2359 of compartment 2358 to secure oxygen scavenger 2455 within an interior volume defined between the two portions or halves 2357, 2359 of the compartment. The two portions or halves 2357, 2359 of compartment 2358 are formed concurrently with the other structures of package 2300 via blow-molding and die-cutting as described with respect to FIGS. 9-10 and package 500. Although shown for use with oxygen scavenger 2455, compartment 2358 may be used to hold or receive other accessories to be used with package 2300 and/or the catheter received therein. For example, compartment 2358 may be configured to hold liquid materials or dry granular materials for use with package 2300 and/or the catheter received therein. Compartment 2358 may be manually closed, or may be mechanically or thermally sealed after any components or accessories are loaded therein. Further, although package 2300 is shown with only one compartment, the package may be formed with multiple compartments for holding multiple accessories for use with package 2300 and/or the catheter received therein.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A package for holding a medical device that includes an elongated shaft, the package comprising:
   a blow-molded one-piece body that defines a spiral lumen configured to receive the elongated shaft of the medical device, the one-piece body having webbing, an upper spiral rib raised in a first direction relative to the webbing, and a second spiral rib raised in a second opposing direction relative to the webbing, wherein the upper and lower spiral ribs collectively form a spiral casing within which the spiral lumen is defined such that webbing extends between adjacent curved portions of the spiral casing.

2. The package of claim 1, wherein the spiral casing has a first end and a second end and the one-piece body includes a loading tube at the second end of the spiral casing, the loading tube defining a lumen configured to receive a distal end portion of the medical device, wherein the lumen of the loading tube is in fluid communication with the spiral lumen of the one-piece body.

3. The package of claim 2, wherein the loading tube is removable and configured to selectively alternate between a first configuration in which a first end of the loading tube is disposed over the second end of the spiral casing and a second configuration in which a second end of the loading tube is inserted into the second end of the spiral casing.

4. The package of claim 2, wherein the lumen of the loading tube has a different cross-sectional shape from the spiral lumen of the spiral casing.

5. The package of claim 2, wherein a cross-sectional shape of the lumen of the loading tube varies along the length thereof.

6. The package of claim 2, wherein the one-piece body further includes a luer retainer formed at the first end of the spiral casing, the luer retainer defining an opening configured to receive a proximal luer fitting of the medical device.

7. The package of claim 1, wherein the spiral casing is a first spiral casing and the one-piece body further includes a second spiral casing that defines a second spiral lumen configured to receive an elongated shaft of a second medical device.

8. The package of claim 7, wherein the second spiral casing is nested within the first spiral casing.

9. The package of claim 1, wherein the spiral lumen of the one-piece body has a non-circular cross-section along at least a portion of its length.

10. The package of claim 1, wherein adjacent curved portions of the spiral casing extend on a common plane.

11. The package of claim 1, wherein the one-piece body further includes at least one of a cannula holder defining an opening configured to receive a cannula for use with the elongated medical device, at least one slot formed through the webbing for attaching an information card thereto, a fastener formed on the webbing for clipping the medical device thereto, and a compartment for clipping an oxygen scavenger.

12. A package for holding a medical device having an elongated shaft and a proximal luer fitting, the package comprising:
   a one-piece body that includes
      a spiral casing formed therein, the spiral casing defining a spiral lumen configured to receive the elongated shaft of the medical device, wherein webbing is disposed between adjacent curved portions of the spiral casing,
      a luer retainer formed at a first end of the spiral casing, the luer retainer defining an opening configured to receive the proximal luer fitting of the medical device, and
      a loading tube formed at a second end of the spiral casing, the loading tube defining a lumen configured to receive a distal end portion of the medical device, wherein the lumen of the loading tube is in fluid communication with the spiral lumen.

13. The package of claim 12, wherein the loading tube is removable and configured to selectively alternate between a first configuration in which a first end of the loading tube is disposed over the second end of the spiral casing and a second configuration in which a second end of the loading tube is inserted into the second end of the spiral casing.

* * * * *